(12) United States Patent
Miller et al.

(10) Patent No.: US 8,172,771 B2
(45) Date of Patent: May 8, 2012

(54) TISSUE COLLECTION SYSTEM

(75) Inventors: Michael E. Miller, Trafalgar, IN (US);
Terry D. Hardin, Irvine, CA (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 771 days.

(21) Appl. No.: 12/030,658

(22) Filed: Feb. 13, 2008

(65) Prior Publication Data
US 2009/0204020 A1 Aug. 13, 2009

(51) Int. Cl.
*A61B 10/00* (2006.01)
*A61M 1/00* (2006.01)
*B01D 35/30* (2006.01)
*B01D 27/00* (2006.01)
*B01D 35/00* (2006.01)
*B01D 35/28* (2006.01)

(52) U.S. Cl. ........ 600/562; 604/317; 604/322; 604/327; 210/232; 210/435; 210/446

(58) Field of Classification Search .......... 600/562–584; 604/319–328, 317, 318; 606/167–173; 210/232, 210/437–439, 446–449, 474, 477, 482
See application file for complete search history.

(56) References Cited

U.S. PATENT DOCUMENTS

| | | | | |
|---|---|---|---|---|
| 3,789,990 A * | 2/1974 | Drori | ............................ | 210/310 |
| 5,223,012 A * | 6/1993 | Best et al. | ........................ | 55/523 |
| 5,397,462 A * | 3/1995 | Higashijima et al. | ......... | 210/136 |
| 5,779,649 A * | 7/1998 | Herbert | .......................... | 600/571 |
| 6,755,802 B2 * | 6/2004 | Bell | .............................. | 604/6.15 |
| 7,226,424 B2 | 6/2007 | Ritchart et al. | | |
| 2005/0049521 A1 | 3/2005 | Miller et al. | | |
| 2006/0260994 A1 | 11/2006 | Mark et al. | | |
| 2007/0149996 A1* | 6/2007 | Coughlin | ...................... | 606/200 |

* cited by examiner

*Primary Examiner* — Max Hindenburg
*Assistant Examiner* — John Pani
(74) *Attorney, Agent, or Firm* — Vista IP Law Group LLP

(57) ABSTRACT

A tissue sample collection device and method are described and disclosed. The tissue sample collection device has a filter that is removably disposed within a sleeve. The filter has an open proximal end and an internal passageway that is in fluid communication with the open proximal end for the passage of fluids. The filter is substantially impermeable to tissue samples but allows the passage of fluids into the internal passageway at a plurality of spaced apart locations along at least a portion of the filter's length. When used to collect tissue samples, the samples are collected on the exterior surface of the filter. Thus, the filter can be removed from the sleeve, and samples can be removed from the exterior surface of the filter. In certain exemplary versions of the tissue sample collection device, the filter is provided on a filter member, and the sleeve is adjustably attached to the filter to define a tissue collection configuration in which the filter is disposed within the sleeve and a tissue retrieval configuration in which filter projects away from the sleeve.

20 Claims, 12 Drawing Sheets

TISSUE COLLECTION SYSTEM

TECHNICAL FIELD

The present disclosure relates to biopsy instruments and methods of taking biopsies. More specifically the present disclosure relates to methods and instruments for the removal of the tissue cores from a biopsy instrument after a sample has been collected.

BACKGROUND

In the diagnosis and treatment of breast cancer, it is often necessary to remove one or more tissue samples from a suspicious mass. The suspicious mass is typically discovered during a preliminary examination involving visual examination, palpitation, X-ray, MRI, ultrasound imaging or other detection means. When this preliminary examination reveals a suspicious mass, the mass must be evaluated by taking a biopsy in order to determine whether the mass is malignant or benign. Early diagnosis of breast cancer, as well as other forms of cancer, can prevent the spread of cancerous cells to other parts of the body and ultimately prevent fatal results.

Where appropriate, a biopsy can be performed by a percutaneous method to avoid the significant trauma and risk of infection to the breast tissue that is caused by the alternative open surgical biopsy procedure. This procedure also reduces the possibility of leaving disfiguring results and minimizes recovery time for the patient. In addition, the patient will incur a lower financial expense because the open surgical technique is more difficult, and time consuming and involves a more complex recovery.

The disadvantages of the open surgical technique coupled with the odds that the lesion is benign present a disincentive for the patient to consent to the biopsy. The added discomfort alone is enough to cause many patients to take the risk that the lesion is benign. The acceptance of this risk can prove to be fatal for the minority of cases where the lesion is malignant. The availability of the percutaneous method further decreases the apprehension of patients and helps insure that they will proceed with receiving the medical care they require.

Percutaneous biopsies have been performed using either Fine Needle Aspiration or core biopsy in conjunction with real-time visualization techniques, such as ultrasound or mammography (X-ray). Fine Needle Aspiration involves the removal of a small number of cells using an aspiration needle. A smear of the cells is then analyzed using cytology techniques. Although Fine Needle Aspiration is less intrusive, only a small amount of cells are available for analysis. In addition, this method does not provide for a pathological assessment of the tissue, which can provide a more complete assessment of the stage of the cancer, if found. In contrast, in core biopsy a larger fragment of tissue can be removed without destroying the structure of the tissue. Consequently, core biopsy samples can be analyzed using a more comprehensive histology technique, which indicates the stage of the cancer. In the case of small lesions, the entire mass may be removed using the core biopsy method. Thus, core biopsy allows the construction of a more detailed picture the disease's progress and type. To further ensure that a complete picture is obtained, it is generally preferable to minimize tissue losses during the retrieval of biopsy cores from the biopsy device.

Certain biopsy devices are configured as an open system where the tissue discharge port is simply an open area of the device. A surgical assistant must remove the tissue from the open compartment using forceps and place the tissue on a sample plate. This ritual must be followed for every sample and, therefore, multiple operators are required. In addition, the open system increases the exposure to potentially infectious materials, and requires increased handling of the sample. As a practical matter, the open system also substantially increases the clean-up time and exposure, because a significant amount of blood and bodily fluid leaks from the device onto the floor and underlying equipment.

Certain closed biopsy devices employ tissue filters that are used to collect tissue samples taken from a patient during the biopsy. In many systems, the tissue filter is generally placed within a filter canister and then tissue is drawn into the interior of the filter by a vacuum source connected to the canister. The tissue is then separated from the fluids that may also be drawn into the canister by the vacuum. Current tissue collection systems are difficult to use and do not provide for easy removal of the resected tissue, or core. In many cases, a retrieval element or scoop is required to remove tissue samples from the interior of the filter. However, the tissue core may be difficult to extract from the interior of the filter. In addition, when there are fine tissues surrounding the filter, the retrieval element may not be able to lift or scrape the fine tissue from the filter wall. In this case, more samples may need to be taken, increasing the trauma to the patient and the potential for infection and other complications. Furthermore, the use of retrieval devices for extracting samples from the interior of a filter may damage tissue samples, resulting in potential loss of valuable information about the sample. Accordingly, a need has arisen for a tissue sample collection device that addresses the foregoing issues.

BRIEF DESCRIPTION OF THE DRAWINGS

Embodiments of the present invention will now be described by way of example in greater detail with reference to the attached figures, in which.

DETAILED DESCRIPTION OF THE INVENTION

Figure 1:
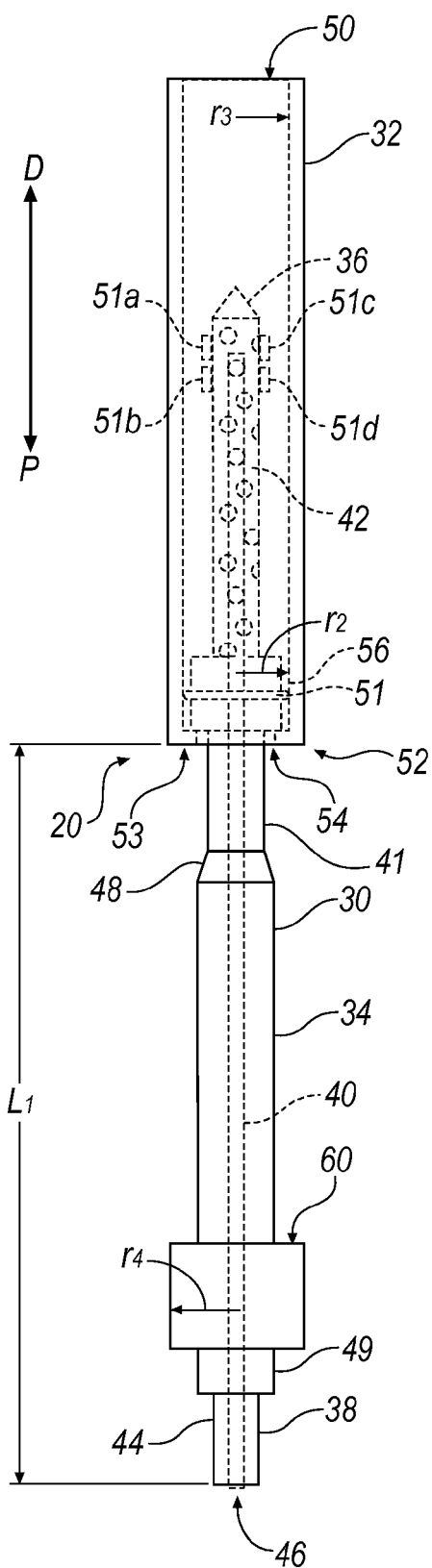
FIG. 1 is a plan view of an exemplary tissue sample collection device in a tissue sample collection configuration.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

Described herein are tissue sample collection devices which are suitable for collecting tissue samples collected from a tissue sample cutting device, in particular, those tissue sample cutting devices used to obtain biopsy samples. In an especially preferred application, the tissue sample collection devices are used to collect breast biopsy samples. As will be discussed in detail below, the tissue sample cutting devices generally include a filter that is removably disposed in a sleeve. The unfiltered tissue and body fluids are collected in the sleeve and filtered to collect tissue cores on the exterior of the filter. Thus, the tissue sample collection devices described herein advantageously avoid the extraction of tissue samples from the interior of a filter, which can lead to undesirable tissue loss and damage.

Figure 2:
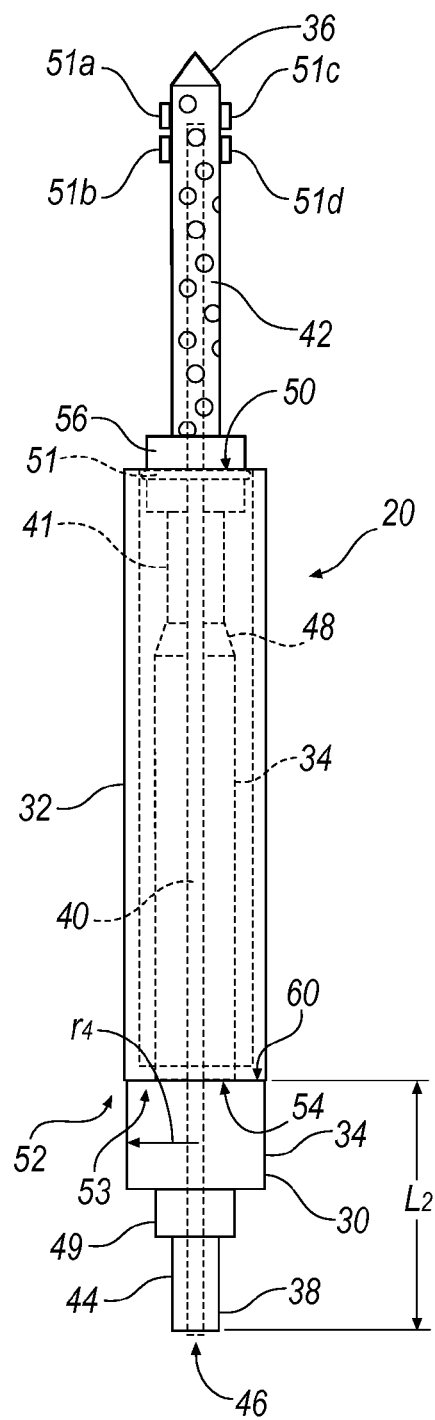
FIG. 2 is a plan view of the tissue sample collection device of FIG. 1 in a tissue sample retrieval configuration.

Referring now to FIGS. 1-2, an exemplary tissue sample collection device 20 is illustrated. Tissue sample collection device 20 is configured to collect biopsy samples such as tissue cores collected from a tissue sample cutting device. In FIG. 1, tissue sample collection device 20 is in a tissue sample collection configuration in which the device 20 receives unfiltered tissue and bodily fluids. In FIG. 2, tissue sample collection device 20 is in a tissue sample retrieval configuration in which collected tissue samples 51a-51d are removed from device 20 for analysis. Tissue sample collection device 20 is preferably configured to be selectively positioned by a user in the tissue sample collection configuration of FIG. 1 and the tissue sample retrieval configuration of FIG. 2.

Tissue sample collection device 20 comprises a generally elongated filter member 30 and a sleeve 32. Filter member 30 is generally cylindrical (or comprises several generally cylindrical sections) in shape and has a proximal end 38 and a distal end 36. Filter 42 is defined along a portion of the length of filter member 30 and is spaced apart from proximal end 38. Filter 42 can be a variety of shapes, including cylindrical, polygonal, conical, frusto-conical, or cylindrical with a frusto-conical, cylindrical, polygonal, pyramidal, or conical distal end 36. In the embodiment of FIGS. 1 and 2, filter 42 is generally cylindrical and includes a conical, closed distal end 36. In certain exemplary embodiments, filter 42 has a length that is less than the length of sleeve 32. In other embodiments, the distance between closed distal end 36 of filter member 30 and open distal end 50 of sleeve 32 when device 20 is in the tissue collection configuration of FIG. 1 is about 10% to about 50% of the length of sleeve 32.

Filter 42 has an exterior surface 45 that is used to collect tissue samples 51a-51d. Internal passageway 40 is defined within filter member 30 and is provided for receiving filtered fluids and discharging them through proximal end 38 to a connected vacuum source. Accordingly, proximal end 38 includes a fluid outlet port 46 and is open. In the illustrative device of FIGS. 1 and 2, filter member distal end 36 is closed, thus preventing the entry of fluids therethrough.

As will be discussed in greater detail below, filter 42 is substantially impermeable to tissue, while being substantially permeable to fluids (liquids and/or gases) such as blood or irrigation fluids (e.g., saline) typically used during biopsy procedures. Sleeve 32 is generally cylindrical and is sized to accommodate filter 42 within its interior. Sleeve 32 may be transparent or translucent so that the user of the tissue sample collection device can see if tissue sample material is present in the sleeve 32. Sleeve 32 has an open distal end 50 and an open proximal end 52 and is configured to slide along a portion of the length of filter member 30. In the tissue sample collection configuration of FIG. 1, filter 42 is preferably entirely disposed within sleeve 32, while in the tissue sample retrieval configuration of FIG. 2, filter 42 is preferably disposed wholly or partially outside of sleeve 32 and projects away from open distal sleeve end 50. Accordingly, tissue samples 51a-51d can be removed from the exterior surface 45 of filter 42 by sliding sleeve 32 along the length of filter member 30 to adjust the configuration of device 20 from the tissue sample collection configuration of FIG. 1 to the tissue sample retrieval configuration of FIG. 2.

To allow device 20 to be repeatably and consistently configured in the configurations of FIGS. 1 and 2, enlarged radially-extending flange or collar 56 is provided adjacent filter 42 to act as an abutment or stop that limits the movement of sleeve 32 in the distal direction (shown as "D" in FIG. 1) with respect to filter member 30. Accordingly, proximal end 52 of sleeve preferably includes a radially-inward facing lip or flange 53 which has a distal facing surface that abuts the proximal facing surface of enlarged flange 56. Because of the inward facing lip 53, proximal end 52 of sleeve 32 has an opening 54 with a radius r1 (FIGS. 3A and 3C) that is less than the radius r2 of enlarged flange 56. In order to allow filter 42 to be slidably removed from sleeve 32 in the distal direction D, open distal end 50 of sleeve 32 is provided with a radius r3 that is substantially equal to or greater than radius r1 of enlarged flange 56. In one embodiment, radii r2 and r3 are sized to accommodate seal 51 between enlarged flange 56 and sleeve 32 while still allowing enlarged flange 56 to slide along the length of sleeve 32. Seal 51 is provided to substantially prevent the leakage of fluid around enlarged flange 56. Suitable exemplary seals include o-ring, polycarbonate, plastic or "windshield wiper" type seals.

As shown in FIGS. 1 and 2, filter member 30 may include a main body 34 that has a wider diameter than intermediate portion 41. Intermediate portion 41 and main body 34 are connected by a frustoconical transition 48. Intermediate portion 41 and filter 42 are connected by enlarged flange 56.

Enlarged, radially-extending flange 60 is provided on filter member 30 between enlarged flange 56 and filter member proximal end 38 to limit the movement of sleeve 32 in the proximal direction (shown as "P" in FIG. 1). Enlarged flange 60 preferably has a radius r4 that is greater than the radius r1 of the proximal end opening 54 of sleeve 32 such that when sleeve 32 is moved in the proximal direction P, the proximal facing surface of lip 53 eventually comes into abutting engagement with the distal facing surface of enlarged flange

60. As FIGS. 1 and 2 indicate, when tissue sample collection device 20 is in the tissue sample collection configuration of FIG. 1, a distance L1 is defined between proximal end 52 of sleeve 32 and proximal end 38 of filter member 30. When tissue sample collection device 20 is in the tissue sample retrieval configuration of FIG. 2, a distance L2 is defined between proximal end 52 of sleeve 32 and proximal end 38 of filter member 38, and L2 is less than L1.

Filter member 30 is preferably configured for connection to a vacuum source (not shown) to aspirate fluids contained in internal passageway 40 out of filter member 30. As a result, proximal end 38 preferably includes an outlet stem or fitting 44, which in FIGS. 1 and 2 is a male fitting through which interior passageway 40 passes. Outlet port 46 is provided and defines an opening through which fluids may pass to a vacuum source. Connection flange 49 is also provided between enlarged radially-extending flange 60 and filter member proximal end 38 to facilitate engagement to a conduit connected to a vacuum source.

Figure 3A:
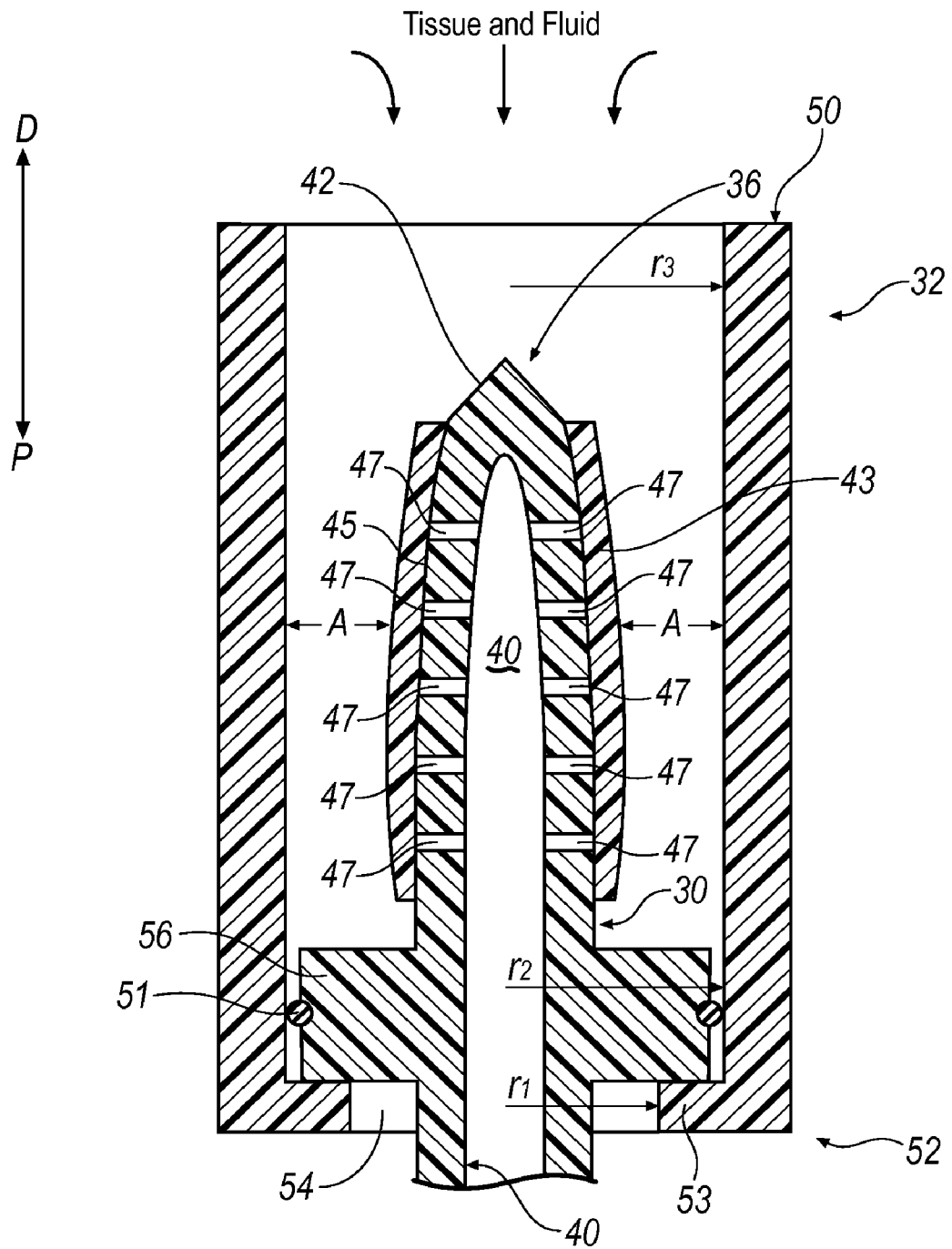
FIG. 3A is an enlarged partial, cross-sectional view through the tissue sample collection device of FIG. 1 showing the device in a tissue sample collection configuration.

As mentioned above, filter 42 is preferably substantially impermeable to tissue samples. However, it is preferably substantially permeable to fluids. Referring to FIG. 3A, a close-up partial cross-sectional view of an exemplary filter member 30 and sleeve 32 is depicted. As the figure indicates, filter 42 includes a plurality of through-holes 47 defined along its length from a point that is proximal of closed distal end 36 to a point that is at or distal of enlarged flange 56. Filter member 30 is preferably constructed of a generally rigid material, including for example a medical grade resin such as a polycarbonate, ABS, or other type of plastic resin. Through holes 47 are provided to facilitate the passage of fluids from a biopsy device through filter 42 and into internal passageway 40. Through holes 47 are spaced apart from one another along the length and around the circumference of filter 42. The size and number of through holes 47 is preferably selected to ensure the collected biopsy cores will be unable to pass through holes 47 while also ensuring that fluids can be reliably aspirated from a biopsy device, through open distal sleeve end 50, into the interior of sleeve 32 through filter 42, into internal passageway 40 and out of outlet port 46 under a selected vacuum pressure.

As discussed previously, filter 42 is preferably substantially impermeable to tissue samples. In some embodiments wherein filter 42 comprises a generally rigid member with holes 47, the holes will be provided in a quantity and size that is sufficient to block the passage of tissue samples while still allowing fluids to be aspirated out of device 20. However, in certain exemplary embodiments, in order to allow for the necessary fluid aspiration, through-holes 47 may be larger than the maximum dimension of many biopsy cores that will be collected. In such cases, filter media 43 (such as a fine mesh material) may be provided and is disposed over through holes 47 to block the passage of tissue samples (e.g., 51*a*-51*d* in FIGS. 1 and 2), through the through holes 47.

When tissue sample collection device 20 is connected to a biopsy device and subjected to a sufficient vacuum pressure at outlet port 46, exterior surface 45 of filter 42 is in direct fluid communication with the opening formed in the open distal end 50 of the sleeve. The term "direct" refers to the fact that the exterior surface 45 is in fluid communication with the opening without the imposition of a filter in between the locations. However, as FIGS. 1 and 2 indicate, exterior surface 45 of filter 42 is not in direct fluid communication with the opening 54 formed in open proximal sleeve end 52 because fluids passing from the region outside of filter exterior surface 45 to internal passageway 40 and opening 54 must pass through holes 47 (or mesh, in the case of the filter 42 of FIG. 3C, described below). Internal passageway 40 is in direct fluid communication with proximal end opening 54. Thus, unfiltered fluids in the sleeve are prevented from exiting sleeve 32 at its open proximal end 52, which could otherwise result in loss of tissue samples, as well as clogging and/or damaging an attached vacuum source. When a sufficient vacuum pressure is applied to internal passageway 40, tissue and fluid located in the annular space "A" defined between the inner surface of sleeve 32 and the exterior surface 45 of filter 42 will be drawn in a radially inward direction toward filter 42. Fluids will pass through filter media 43 and through through-holes 47 to enter internal passageway 40. Tissue samples 51*a*-51*d* will not pass though the filter media 43, but will instead be collected on exterior surface 45 of filter 42 (or on filter media 43, if present). Thus, a fluid path is defined from the open distal end 50 of sleeve 32 to annular space A, through holes 47, through internal passageway 40 and through filter member outlet port 46 and sleeve proximal end opening 54. However, as indicated previously, fluid is substantially prevented from flowing directly between the annular space A and proximal sleeve opening 54. In certain methods of use, internal passageway 40 of filter 42 will be subjected to a pressure of from about 15 in. Hg to about 30 in. Hg. In certain preferred methods, a pressure of from about 18 to about 22 in. Hg. is used, and in an especially preferred method, a pressure of about 20 in. Hg. is used.

In certain exemplary embodiments, filter 42 has a maximum outer diameter that is about 20% to about 80%, and more preferably from about 55% to about 65% of the inner diameter of sleeve 32. In one exemplary embodiment, the maximum outer diameter of filter 42 is about 61% of the inner diameter of sleeve 32, and the annular space A defined between filter member 30 and the interior of sleeve 32 is about 0.11 inches. However, the annular spacing A is preferably no less than the size of the biopsy cores entering sleeve 32 to prevent the annular space A from becoming clogged.

Figure 3B:
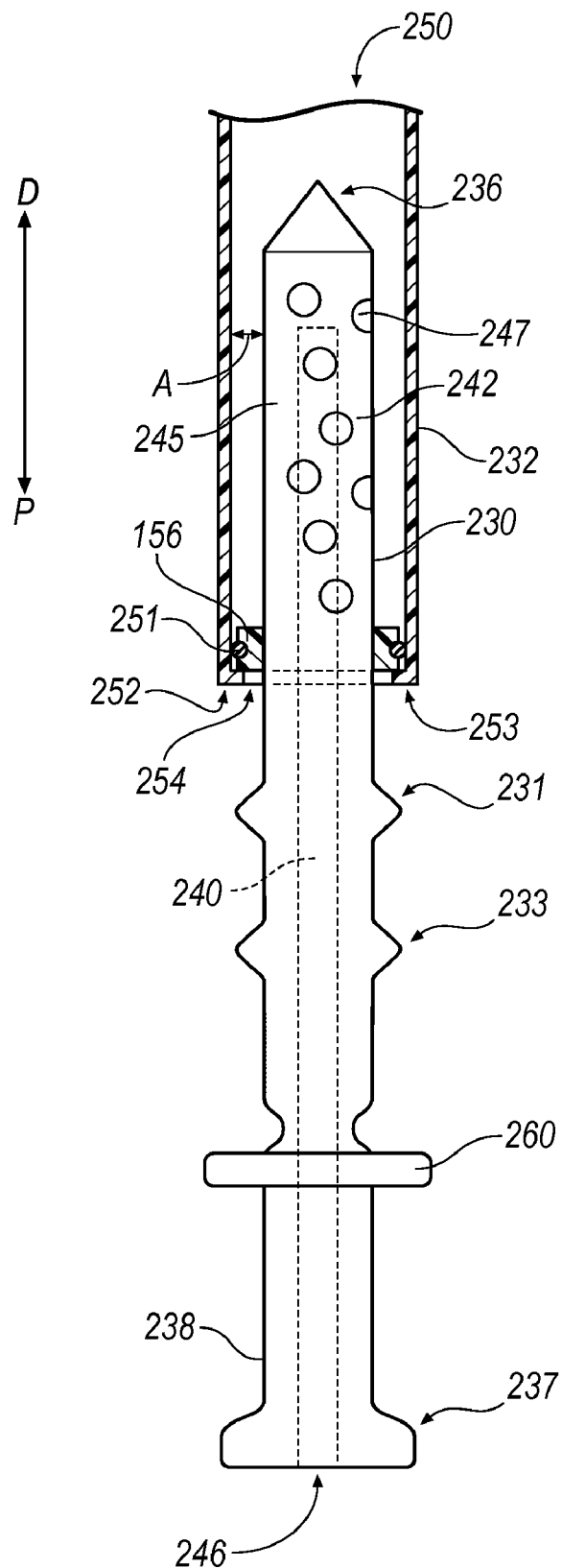
FIG. 3B is an alternate embodiment of the tissue sample collection device of FIGS. 1 and 2 shown in a tissue sample collection configuration.

An alternate embodiment of tissue sample collection device 20 is depicted in FIG. 3B. As with the embodiment of FIGS. 1 and 2, the device 20 of FIG. 3B has a tissue sample collection configuration and a tissue sample retrieval configuration. However, only the tissue sample collection configuration is depicted. Sleeve 232 is generally cylindrical and is designed in the same manner as sleeve 32 in FIGS. 1 and 2. Filter member 230 includes open proximal end 238 and closed distal end 236. Filter 242 is provided along a portion of the length of filter member 230 and is located adjacent filter member closed distal end 236 and spaced apart from filter member open proximal end 238. Filter 242 is substantially similar to filter 42 in FIGS. 1 and 2 and is substantially impermeable to tissue samples while being substantially permeable to fluids.

Radially-extending flange 256 is provided adjacent filter 242 to limit the movement of sleeve 232 in distal direction D. Radially-inwardly facing lip or flange 253 is integrally formed with sleeve 232 and provides a distally-facing surface that abuttingly engages the proximally-facing surface of filter member flange 256 to restrict the movement of sleeve 232 in the distal direction D with respect to filter member 230. Flange 256 preferably has a diameter greater than the diameter of opening 254 formed in the proximal end 252 of sleeve 232. As with the embodiment of FIGS. 1 and 2, filter 242 collects tissue samples on its exterior surface 245 while allowing fluids to pass through holes 247 (not shown) and filter media 243 (if provided) into internal passageway 240 and ultimately out of port 246.

Radially-extending flange 260 is provided between radially-extending flange 256 and proximal end 238 of filter member 230 to limit the movement of sleeve 232 in proximal direction P with respect to filter member 230. Flange 260 preferably has a diameter that is greater than the diameter of opening 254 in open proximal end 252 of sleeve 232. In the embodiment of FIG. 3B, the diameter of flange 260 is also greater than the outer diameter of sleeve 232 at its proximal end 252. As will be discussed below, the tissue sample collection devices described herein may be installed in a housing that provides fluid connections to a biopsy device and a vacuum source. The housing will preferably be shaped to substantially conform to the contour and shape of the tissue sample collection device (e.g., the tissue sample collection device 20 of FIGS. 1-2, the tissue sample collection device 220 of FIG. 3A, etc.). To provide for secure retention and accurate installation of tissue sample collection device 220 in a housing, additional features may be defined on the surface of filter member 230 which cooperate with corresponding features in the housing. In the embodiment of FIG. 3B, ridges 231 and 233 are provided around the circumference of filter member 230 and are spaced apart from one another along the length of filter member 230 to facilitate retention in a housing. Enlarged proximal end section 237 is another feature that may be provided to facilitate such retention. Instead of surface features that project away from filter member 230 (such as ridges), filter member 230 may also be provided with recessed regions, such as grooves, which cooperate with corresponding projections formed in the housing.

Figure 3C:
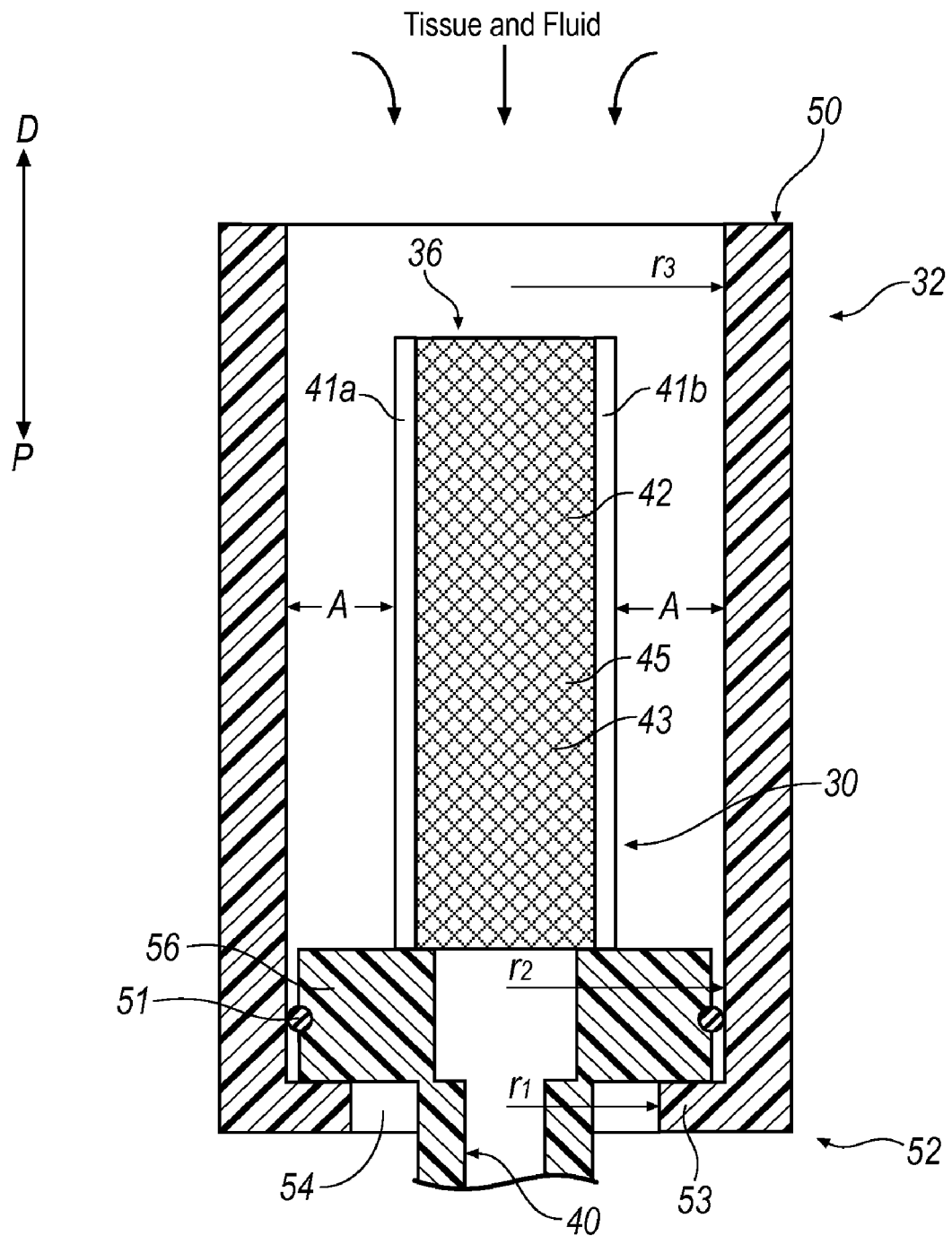
FIG. 3C is an alternate embodiment of the tissue sample collection device of FIGS. 1, 2, and 3A in which the filter comprises a reinforced mesh.

Referring to FIG. 3C, a partial, cross-sectional view of an alternate version of filter member 30 from FIGS. 1, 2, and 3A is depicted. In FIG. 3C, filter member 30 includes the same features as filter member 30 depicted in FIGS. 1 and 2, except that filter 42 has been modified. Filter shapes such as conical, frusto-conical, polygonal, or pyramidal shapes may be used. However, in FIG. 3C, filter 42 is a generally cylindrical body spaced apart from proximal end 38 of filter member 30. Filter 42 includes a closed distal end 36 spaced apart from open distal end 38 of filter member 30. Annular space A is defined between supports 41a/41b and sleeve 32. Instead of a rigid body with through-holes, filter 42 comprises a cylindrical mesh 43 to which supports 41a and 41b are attached. Supports 41a and 41b are longitudinally extending members that are spaced apart from one another around the circumference of filter 42. In the embodiment of FIG. 3C, two (2) supports are provided. However, additional supports may be provided, and in one exemplary configuration, four (4) supports are provided in which each pair comprises two (2) supports placed in diametrically facing opposition to one another. Closed distal end 36 comprises a generally thin cylindrical structure attached to the distal ends of supports 41a and 41b. A variety of mesh 43 materials may be used. The mesh 43 is preferably selected to reliably allow fluids to pass through it while substantially preventing tissue samples from passing through. In addition, the mesh 43 preferably avoids premature clogging so that a desired biopsy procedure may be completed before removing filter 42 to retrieve tissue samples 51a-51d. In one exemplary configuration, a hemodialysis grade, 240 micron filter mesh is used. Flange 56 is provided adjacent the proximal end of filter 42. Filter 42 includes interior passageway 40 through which filtered fluids pass to ultimately exit filter member 30 at port 46. Supports 41a/41b, flange 56, and closed distal end 36 preferably comprise a generally rigid polymeric material such as a polycarbonate, ABS, or plastic. Supports 41a and 41b are preferably configured and sized to prevent the mesh comprising filter 42 from collapsing when in use. Seal 51 is provided to prevent leakage of fluid and/or tissue around flange 56 while allowing filter 42 to slide within sleeve 32.

Figure 4:
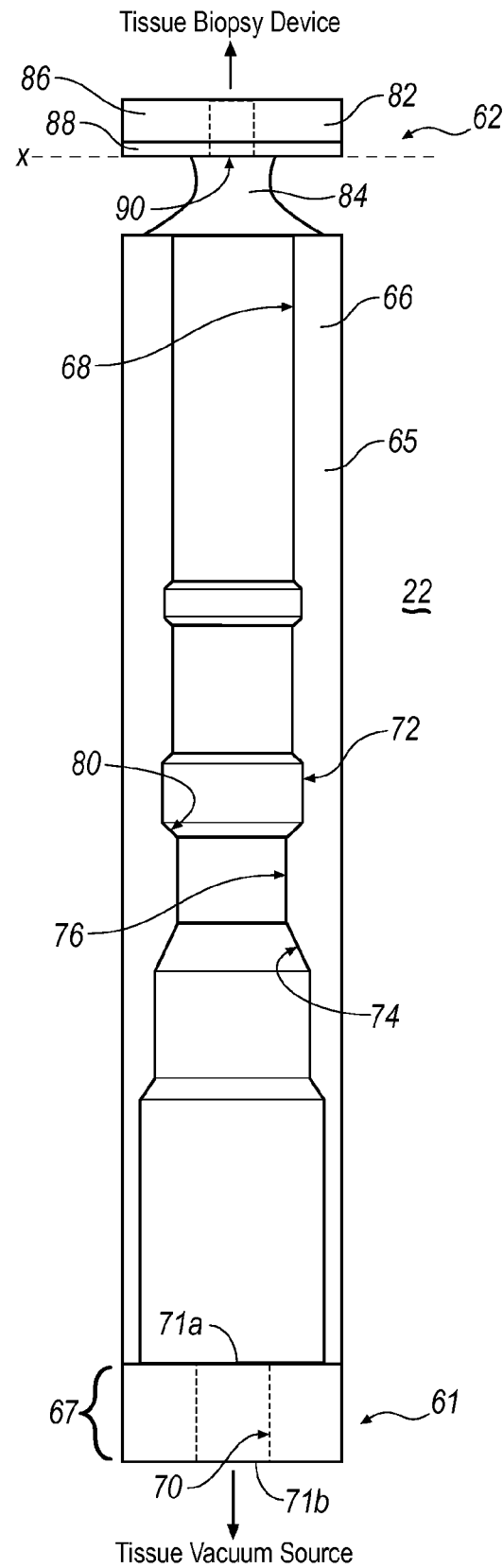
FIG. 4 is a plan view of an exemplary housing for a tissue sample collection device.

As indicated above, in certain exemplary systems, the tissue sample collection devices described herein are configured for attachment to a housing. The housing provides a means of selectively attaching and fluidly coupling the tissue sample collection device to a tissue sample cutting device, such as those used to perform biopsy procedures. Referring to FIG. 4, an exemplary tissue sample collection device housing is illustrated. Housing 22 is a generally elongated structure with a proximal end 61 and a distal end 62. Housing 22 comprises a main body 66 and lid 82. Housing 22 also preferably has an open face 65 along its length into which a tissue sample collection device may be inserted. For purposes of illustration, tissue sample collection device 20 will be described. However, it should be understood that a variety of other tissue sample collection devices, including without limitation tissue sample collection device 220 (FIG. 3B) may be used.

In the embodiment of FIG. 4, housing 22 is a semi-cylindrical structure such as would be produced by removing a longitudinal cross-section from a cylinder. As a result, housing 22 partially encloses the perimeter of tissue sample collection device 20 along its length. In the view of FIG. 4, the open face 65 of housing 22 is visible. A closed face of housing 22 would be seen from the opposite side of the figure.

Referring again to FIG. 4, main body 66 of housing 22 has a cavity 68 defined within open face 65 for receiving tissue sample collection device 20. Cavity 68 is preferably proportioned and shaped to accept and cradle the tissue sample collection device 20 as shown in FIG. 5 and described later. As further illustrated in FIG. 4, proximal end 61 of housing 22 defines a closed cylindrical structure 67 configured to fully enclose filter outlet fitting 44 and connection flange 49. Proximal end 61 also includes a bore 70, which receives outlet fitting 44 through bore distal opening 71a. Bore proximal opening 71b is preferably sized to accommodate vacuum system tubing with a suitable attachment fitting. Thus, housing 22 preferably allows fluids aspirated from tissue sample collection device to pass through bore 70 and into a vacuum system while substantially preventing fluid leakage from bore 70. The cavity 68 is also provided with various cutaways, such shown at 72 and 74, and reduced diameter portions, such as shown at 76, to accommodate the shape of the tissue sample collection device 20.

The main body 66 is also provided with one or more abutments, such as abutment 80, which cooperate with and engage a corresponding surface on filter member 30 to restrain the movement of filter member 30 in the proximal direction P and/or distal direction D. In the embodiment of FIG. 4, abutment 80 engages proximal end 52 of sleeve 32. Thus, in addition to holding the tissue sample collection device 20 in place, the engagement of housing abutment 80 and sleeve proximal end 52 maintains tissue sample collection device 20 in the tissue sample collection configuration of FIG. 1 when the tissue sample collection device 20 is in an installed condition in housing 22. When tissue sample collection device 20 is installed in housing 22, device 20 and housing 22 define a tissue sample collection device assembly 10.

Figure 5A:
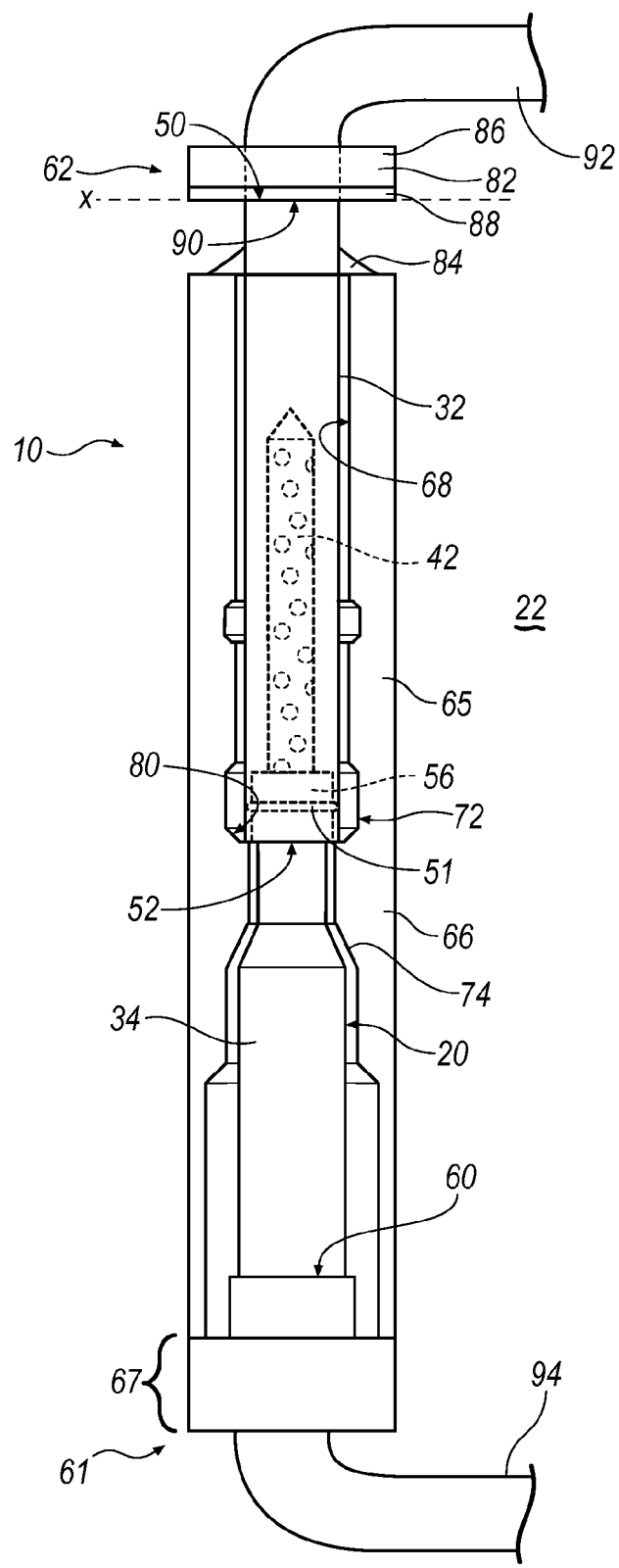
FIG. 5A is a plan view of the tissue sample collection device of FIG. 1 installed in the housing of FIG. 4.
Figure 5B:
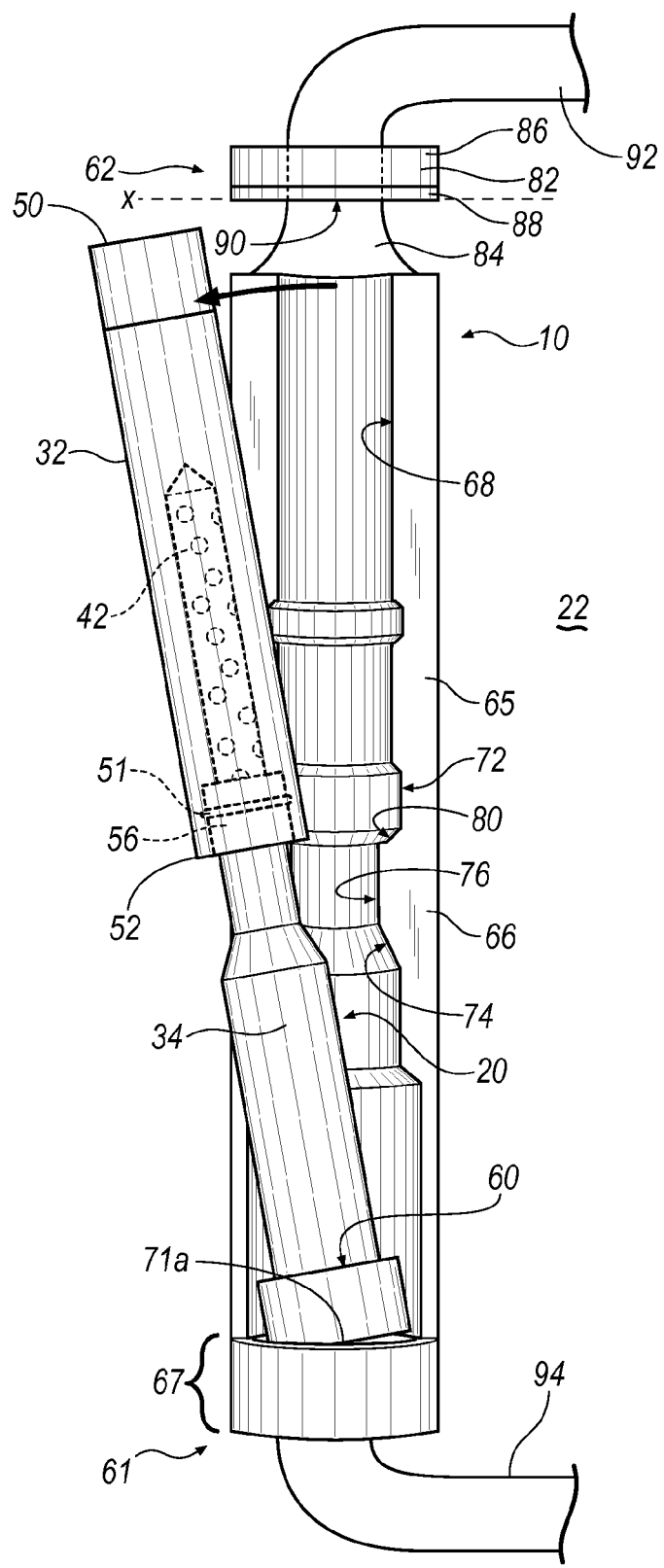
FIG. 5B is a perspective view of the housing of FIG. 4 depicting the insertion of the tissue sample collection device of FIG. 1 into the housing.

As shown in FIGS. 4, 5A, and 5B, housing 22 is provided with a lid 82 to selectively attach sleeve open distal end 50 to a tissue sample cutting device. Lid 82 may be completely detachable from housing 22. However, it is preferably attached to housing 22 so as to be selectively engageable with tissue sample collection device 20. In one embodiment, lid 82 is connected to main body 66 by a mechanical hinge. However, in a more preferred embodiment, and as illustrated in FIGS. 4, 5A, and 5B, lid 82 is connected to the housing 22 by a "living" hinge 84. As is known to those skilled in the art, a living hinge is a hinge defined by a thinning of material, such as a plastic material, which allows parts to remain integrally formed with and connected to one another, while still allowing one part to move with respect to the other. Thus, in the embodiment of FIGS. 4, 5A, and 5B, lid 82 is pivotable about an axis x that is substantially perpendicular to the longitudinal axis of housing 22. Lid 82 is biased into the closed position of FIGS. 4 and 5A, but may be pivoted into the open position by a user. Housing may be made from a variety of known materials, but is preferably constructed of a medical grade resin, such as by molding a polycarbonate, ABS, or other type of plastic resin.

The lid 82 includes a seat 86 and a seal ring 88. An inlet port 90 is formed in the seat 86. A supply line 92, shown in FIGS. 5A and 5B is connected to the inlet port 90 to connect the sleeve to a source of tissues sample material, such as a tissue sample cutting device, not shown.

A method of using the tissue sample collection device 20 and housing 22 to collect and remove tissue samples will now be described. FIG. 5A depicts tissue sample collection device 20 in an installed condition in housing 22. FIG. 5B shows tissue sample collection device 20 and housing 22 from a perspective view during the installation of tissue sample collection device 20 into housing 22. In a preferred method of installation, tissue sample collection device 20 is adjusted to the tissue sample collection configuration of FIG. 1. Tissue sample collection device 20 is then seated in the housing 22 by inserting the outlet stem 44 into the bore 70 of the housing 22 as shown in FIG. 5B. At this point, tissue sample collection device 20 is pivoted away from the longitudinal axis of housing 22 and away from lid 82. Tissue sample collection device 20 is then pivoted toward lid 82 and the longitudinal axis of housing 22 until it is seated position in the cavity 68. Vacuum supply conduit 94 is connected to bore 70 and may also be connected directly to filter member outlet stem 44 within bore 70 to connect filter member internal passageway 40 to a source of vacuum, not shown. The removable lid 82 is attached to the open distal end 50 of sleeve 32 such that the open distal end 50 is in fluid communication with housing port 90. The engagement between open distal sleeve end 50 and port 90 is preferably such that fluids passing through lid 82 and into sleeve 32 will substantially not leak from lid 82 or sleeve 32. Port 90 is connected to a source of tissue sample material, such as a biopsy device, via conduit 92, which is preferably a flexible hose or tubing. The user turns on the source of vacuum and uses the biopsy device to cut a tissue sample. In one exemplary embodiment, the biopsy device comprises an inner tissue cutting cannula disposed in an outer cannula such that the inner tissue cutting cannula can translate and rotate within the outer cannula. In accordance with this embodiment, conduit 92 is in fluid communication with the inner cannula to receive aspirated tissue samples and fluid. As tissue samples are severed by the inner cannula, tissue samples and fluid are received through conduit 92, port 90, and into open distal end 50 of sleeve 32. The tissue and fluid is then drawn in a radially inward direction toward filter 42. However, tissue samples 51*a*-51*d* will be collected on exterior filter surface 45 and will be prevented from passing through filter 42.

Once the desired tissue samples are collected, the vacuum source is turned off. Lid 82 is pivoted into the open position, and tissue sample collection device 20 is pivoted away from lid 82 and the longitudinal axis of housing 22. Outlet fitting 44 is then removed from bore 70 of housing 22, and the tissue sample collection device is removed from housing 22. Sleeve 32 is then slid in the proximal direction until sleeve lip 53 abuts radially-extending flange 60 to adjust device 20 from the tissue sample collection configuration of FIG. 1 into the tissue sample retrieval configuration of FIG. 2. Tissue samples 51*a*-51*d* are then removed from exterior surface 45 of filter 42 for subsequent testing and/or analysis.

Figure 6:
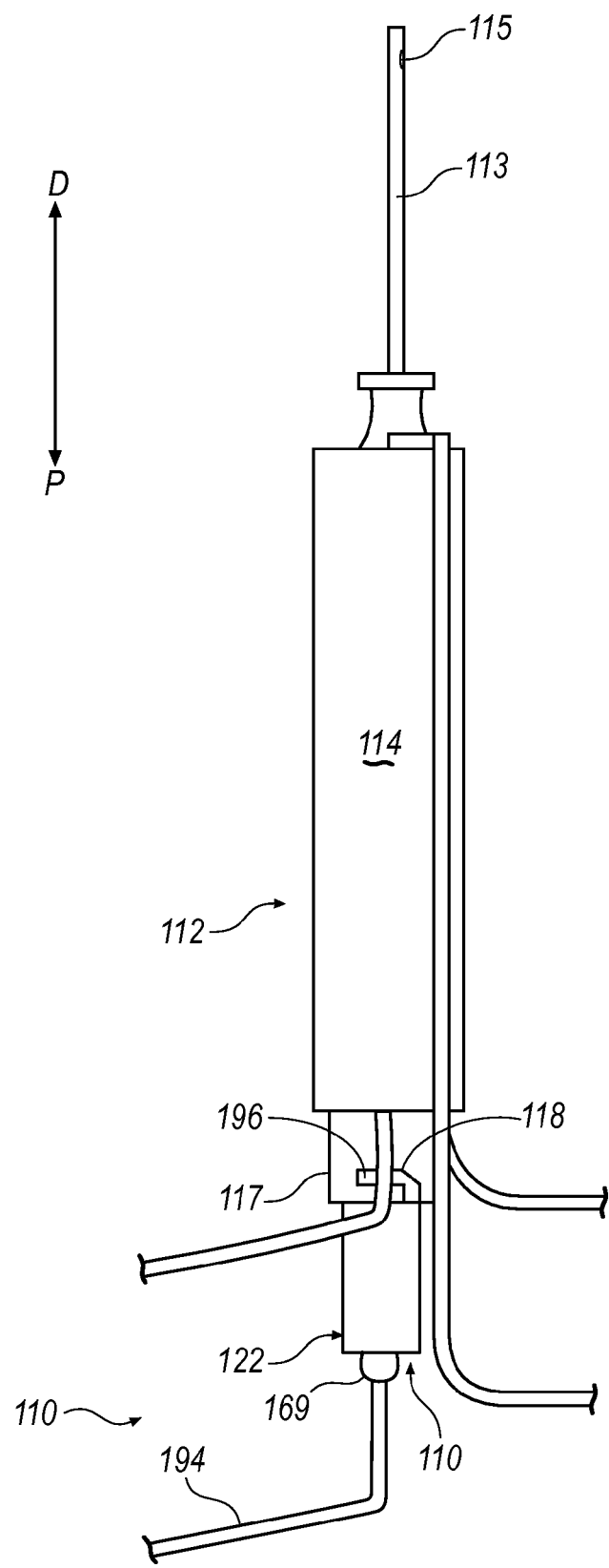
FIG. 6 is a plan view of an alternate exemplary tissue sample collection device installed on a tissue sample cutting device.
Figure 7:
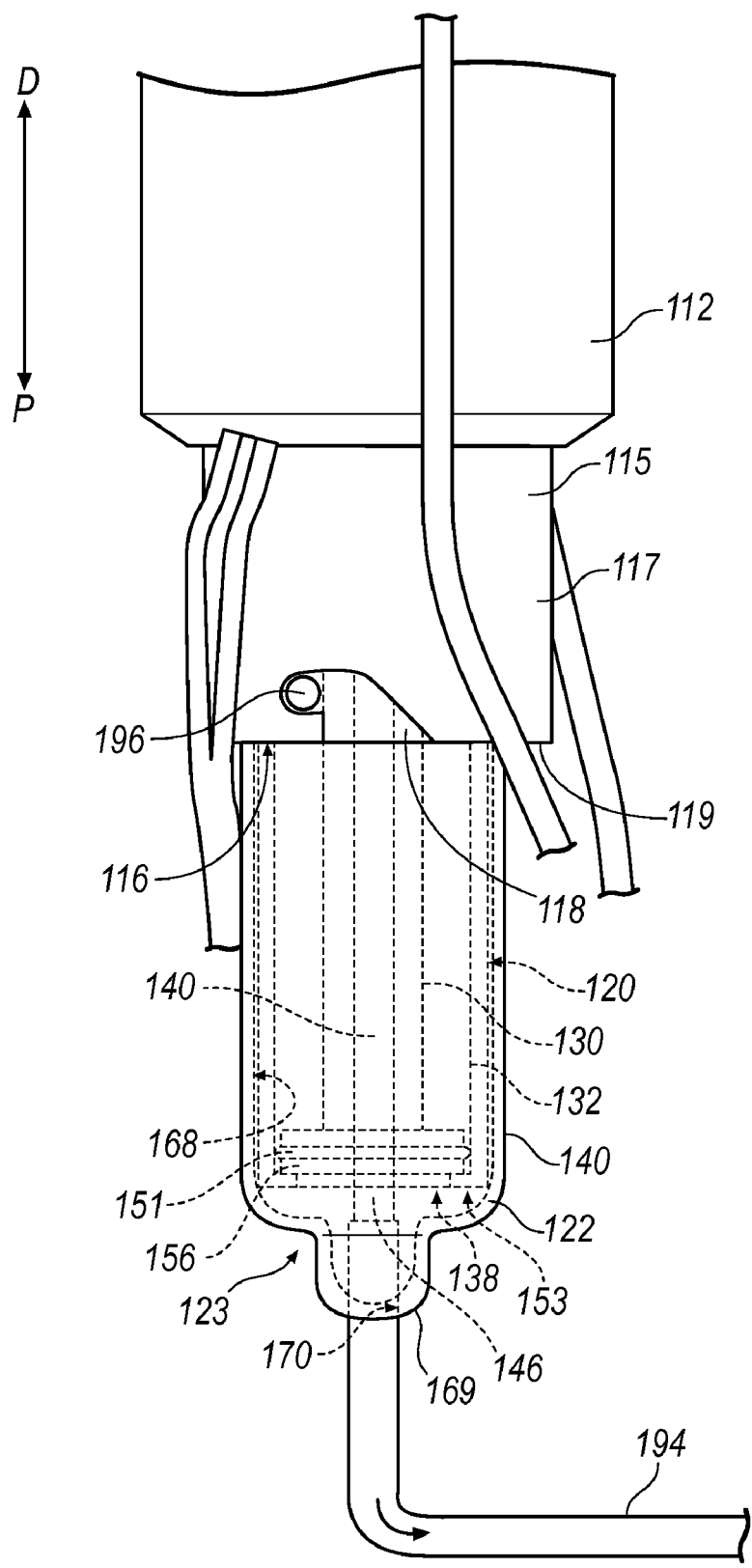
FIG. 7 is an enlarged partial plan view of a tissue sample collection device assembly comprising the tissue sample collection device of FIG. 6 installed on a tissue sample cutting device.
Figure 8A:
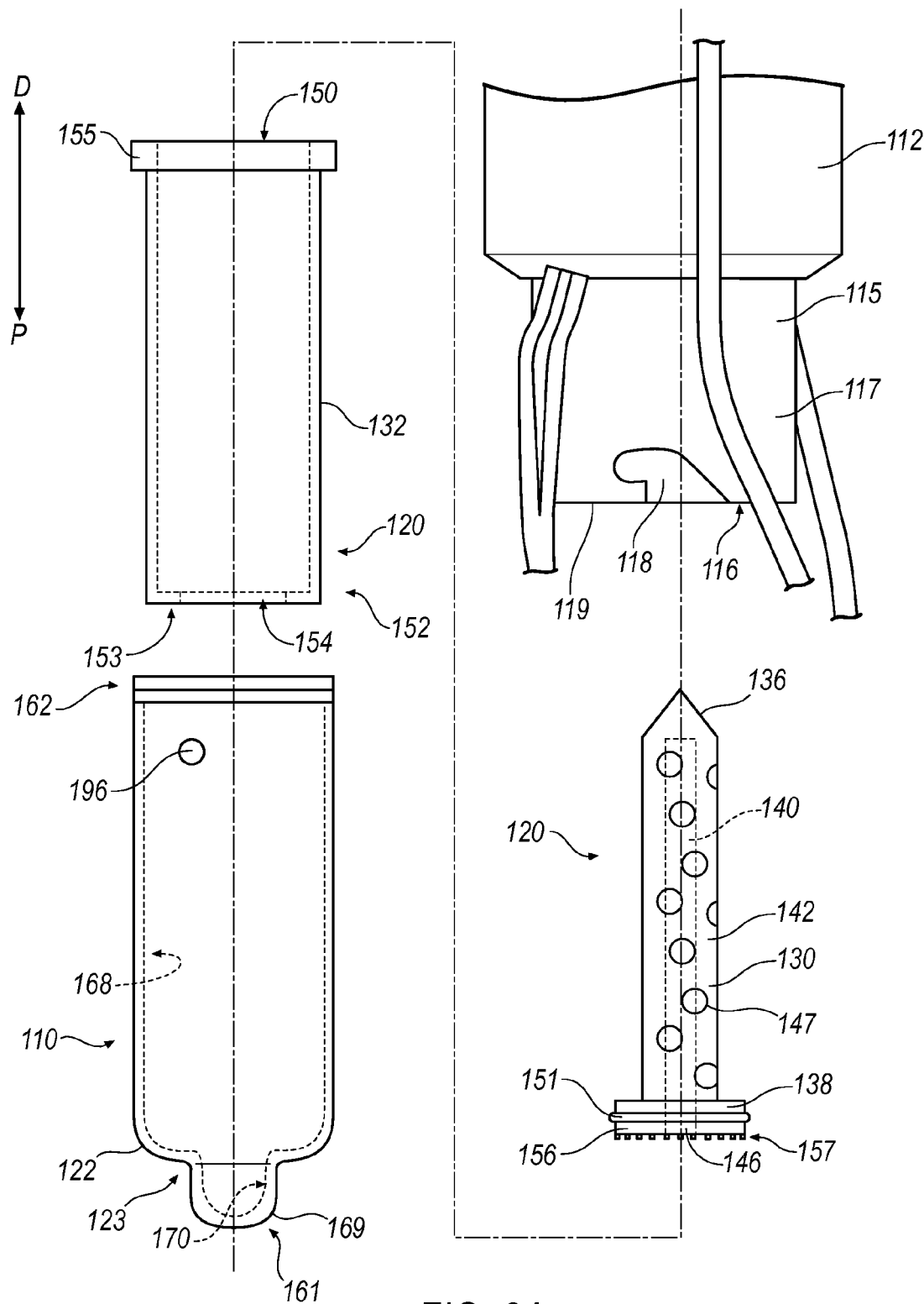
FIG. 8A is an exploded view of the tissue sample collection device assembly and tissue sample cutting device of FIGS. 6 and 7.
Figure 8B:
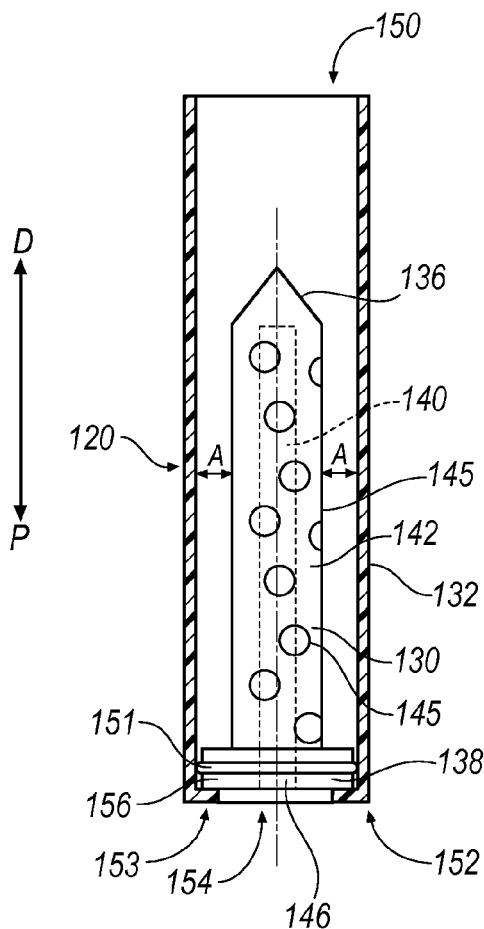
FIG. 8B is a plan view of the tissue sample collection device of FIGS. 6, 7, and 8A.

Referring now to FIGS. 6, 7, 8A, and 8B, an alternative exemplary tissue sample collection device 120 is illustrated. As best seen in FIG. 8B, tissue sample collection device 120 comprises filter member 130 and sleeve 132. Filter member 130 is removably disposed within the interior of sleeve 132.

Sleeve 132 is generally of the construction described previously with respect to the embodiment of FIGS. 1-5B. Sleeve 132 is generally cylindrical and comprises an open proximal end 152 and an open distal end 150. At open proximal end 152, a radially-inward projecting flange defines a lip 153. Lip 153 aids in retaining filter member 130 within sleeve 132 during the collection of tissue samples. The lip 153 defines an opening 154 in proximal end 152 having a diameter less than that of the opening defined by open distal end 150. At open distal end 150 a radially-outward projecting flange defines a lip 155.

Filter member 130 is a generally rigid elongated member constructed of a medical grade resin or other suitable material and comprising a base 156 and a filter 142. Filter member 130 has an internal passageway 140 defined along at least a portion of its length between a closed distal end 136 and an outlet port 146 that defines an open proximal end 138. In certain exemplary embodiments, filter 142 has a length that is less than the length of sleeve 132. In other embodiments, the distance between closed distal end 136 of filter member 130 and open distal end 150 of sleeve 32 when device 120 is in the tissue collection configuration of FIG. 8B is about 10% to about 50% of the length of sleeve 132. Filter 142 has a plurality of spaced apart holes 147 along at least a portion of its length. The holes 147 may be sized to substantially prevent the passage of tissue samples while allowing the passage of fluids. However, filter media 143 (not shown) such as a mesh may also be provided and disposed over holes 147. Thus, filter 142 is substantially impermeable to tissue samples. Filter 142 has an exterior tissue collecting surface 145 that captures tissue samples when tissue sample collection device 120 is connected to a tissue sample cutting device. In certain embodiments, filter 142 has a maximum outer diameter that is from about 20% to about 80%, and more preferably from about 55% to about 65%, of the inner diameter of sleeve 132. In one exemplary embodiment, the maximum outer diameter of filter 142 is about 61% of the inner diameter of sleeve 132, and the annular space defined between filter member 130 and sleeve 132 is about 0.11 inches. However, the annular spacing is preferably no less than the size of the biopsy cores entering sleeve 132 to prevent the annular space A (FIG. 8*b*) from becoming clogged.

Base 156 has a diameter that is larger than the diameter of filter 142 but which is substantially equal to or slightly less than the inner diameter of sleeve 132 so as to allow filter member 132 to be slidingly inserted into and removed from sleeve 132. Base 156 may be provided with seal 151 to inhibit leakage of fluid from filter member 130 through sleeve proximal end opening 154. As indicated in FIG. 8B, lip 153 prevents filter member 132 from falling out of sleeve 132 in the proximal direction. As a result, filter member 130 is insertable through open distal end 150 of sleeve 132, but is not insertable through open sleeve proximal end 152. Thus, in the tissue sample collection configuration of FIG. 8B, filter member base 156 is located closer to sleeve proximal end 152 than is the closed distal end 136 of filter 142. When a vacuum pressure is applied to internal passageway 140 of filter member 130 through port 146, tissue and fluids present in the annular space A defined between sleeve 132 and filter 142 are drawn in a radially inward direction, thereby causing tissue samples to be collected on filter exterior surface 145 while allowing fluids to pass through filter media 143 (if present) and holes 147 to enter internal passageway 140. As FIG. 8B indicates, filter exterior surface 145 is in direct fluid communication with sleeve open distal end 150 but is substantially not in direct fluid communication with sleeve open proximal end 152 because fluids must pass through holes 147 to reach open proximal end 152 and its opening 154. Thus, when tissue sample collection device 120 is installed as shown in FIG. 8B, a fluid path is provided from the open distal end 150 of sleeve 132, through holes 147, into internal passageway 140, and through outlet port 146. However, there is no direct fluid path from annular space A to the opening 154 formed in the proximal end 152 of sleeve 132. Internal passageway 140 is in direct fluid communication with proximal end opening 154. As shown in FIG. 8A, base 156 may optionally be configured to reduce the surface area contact between base 156 and the distal facing surface of sleeve lip 153. In FIG. 8A, the proximal facing surface of base 156 comprises a plurality of spaced apart protrusions or teeth 157 (not shown in FIG. 8B) which engage the distal facing surface of lip 153. The use of a reduced contact area reduces the likelihood that filter member 130 will stick to sleeve lip 153, which could otherwise result in the trapping of fluids between base 156 and sleeve 132 and/or the reduction of vacuum. Although a plurality of protrusions 157 is shown in FIG. 8A, a variety of other surface geometries may be used to create a non-smooth proximal facing surface of base 156.

Referring again to FIG. 8A, in a preferred embodiment, tissue sample collection device 120 is connected to a tissue sample cutting device via a housing 122 that is selectively attachable to tissue sample cutting device 112. Housing 122 is generally cylindrical in shape and sized to accommodate all or a portion of the length of sleeve 132 within its interior. Housing 122 has a proximal end 161 and a distal end 162. In one exemplary embodiment, housing 122 includes a fitting 169 for connecting housing 122 to a vacuum source conduit 194 (FIG. 7). Fitting 169 has a bore 170. When sleeve 132 and filter member 130 are installed in housing 122, bore 170 is in fluid communication with filter member port 146 and internal passageway 140 to thereby place the vacuum source conduit in fluid communication with internal passageway 140. Fitting 169 may be configured as a male or female fitting for connecting to a suitably configured vacuum source conduit 194. Instead of using cylindrical housing 122, a housing having the semi-cylindrical design of FIG. 4 may also be used. In that case, filter member 130 may optionally be provided with a proximal end fitting for fluidly connecting member 130 to the proximal end of the housing, which can in turn be fluidly connected to a source of vacuum.

In the embodiment of FIG. 8A, filter member 130, sleeve 132, and housing 122 are configured to be assembled and define a tissue sample collection assembly 110 that can be installed as an integral assembly on a tissue sample cutting device, such as a biopsy device. Open proximal end 162 of housing 122 engages the proximal facing surface of sleeve lip 155 to restrain the movement of sleeve 132 with respect to housing 122 in proximal direction P. When sleeve 132 is inserted into housing 122, a user can remove sleeve 132 by gripping lip 155 and sliding sleeve 132 in distal direction D with respect to housing 122.

In certain preferred embodiments, housing 122 has a defined surface feature that engages a complementary feature on a tissue sample cutting device to thereby retain the tissue sample collection device to it. Referring to FIGS. 6, 7, and 8A, a tissue sample cutting device 112 is provided which comprises a handpiece 114 and an outer cannula 113. In one preferred embodiment, an inner cutting cannula 116 (not shown) having an inner lumen is movably disposed within the outer cannula 113 and is translatable in a direction along the longitudinal axis of the outer cannula. Inner cutting cannula 116 may also be co-axially rotatable about the longitudinal axis of the outer cannula 113. Examples of tissue sample cutting devices that may be used include those disclosed in U.S. patent application Ser. No. 10/958,026, the entire contents of which are hereby incorporated by reference. In certain exemplary embodiments, the inner cutting cannula is configured to sever tissue samples that prolapse into a tissue receiving port 115 formed in outer cannula 113. When the tissue sample collection device assembly 110 (i.e., sleeve 132, filter member 130, and housing 122) is connected and installed on tissue sample cutting device 112, sleeve open distal end 150 is preferably in fluid communication with the inner lumen of inner cutting cannula 116 to receive tissue and fluid samples aspirated therethrough.

As best seen in FIGS. 7 and 8A, tissue sample cutting device 112 comprises a proximal hub 117. Proximal hub 117 is a generally cylindrical structure having an open proximal end 119 which is configured to receive tissue sample collection device assembly 110 in its interior. Proximal hub end 119 may include one or more contoured engagement grooves 118 which engage complementary projections 196 (e.g., bosses or pins) formed on housing 122. As indicated in FIGS. 7 and 8A, the engagement of projections 196 and contoured grooves 118 is such that the tissue sample collection device assembly 110 is substantially prevented from moving in either the proximal or distal direction with respect to tissue sample cutting device 112. In the configuration of FIG. 7, open distal end 150 of sleeve 132 is sealingly engaged with tissue sample cutting device 112 so as to be in fluid communication with the inner cutting cannula 116 while substantially preventing leakage of fluid or tissue from proximal hub 117.

A method of using the tissue sample collection device 120 and assembly 110 depicted in FIGS. 6, 7, 8A, and 8B will now be described. In accordance with the method, tissue sample collection device 120 is assembled into a tissue sample collection configuration by inserting filter member 130 into open distal end 150 of sleeve 132 such that base 156 enters sleeve 132. Filter member 130 is then slid in the proximal direction until the proximal facing surface of base 156 seats against the distal facing surface of sleeve proximal lip 153 as shown in FIG. 8B. Thus configured, tissue sample collection device 120 is then inserted into open distal end 162 of housing 122 such that sleeve proximal end 152 enters housing 122 before sleeve distal end 150. To assemble tissue sample collection device assembly 110, tissue sample collection device 120 is slid within housing 122 until sleeve proximal end 152 engages tapered region 123 which prevents further proximal movement of sleeve 132 with respect to housing 122. In certain embodiments, sleeve distal end 150 may project outside and away from housing distal end 162 at this point, while in other embodiments it may be disposed within housing 122. However, in the embodiment of FIG. 8A, lip 155 engages housing distal end 162 such that only lip 155 projects distally away from housing 122. Tissue sample collection device assembly 110 is then inserted into open proximal hub end 119 such that sleeve distal end 150 and housing distal end 162 enter proximal hub end 119. During this insertion step, projections 196 formed on housing 122 are aligned with engagement grooves 118. Housing 122 is then rotated to engage projections 196 with grooves 118 as shown in FIG. 7. Either prior to or after inserting housing 122 into proximal hub opening 119, vacuum conduit 194 is connected to fitting 169.

The user turns on the source of vacuum and uses the tissue sample cutting device 112 to cut a tissue sample. During the tissue cutting procedure, tissue and fluid are aspirated through the inner cannula of tissue sample cutting device 112 and into open distal end 150 of sleeve 132. Tissue and fluid present in the annular space A defined between filter 142 and the interior surface of sleeve 132 (FIG. 8B) are then drawn radially inward to filter 142. Fluid passes through filter media 143 (if present) and holes 147 to enter internal passageway 140. However, tissue samples (not shown) are collected on exterior surface 145 of filter 142. Fluids entering internal passageway 140 then exit filter member 130 at port 146 and exit bore 170 defined in housing proximal end fitting 169. The filtered fluids then exit tissue sample collection device assembly 110 and enter vacuum supply conduit 194.

Once a tissue sample is collected in the sleeve 132 and the vacuum has been turned off, the filter housing 122 is decoupled from the tissue sample cutting device 112 and the tissue sample collection device 120 is removed from the filter housing 122. The sleeve 132 may then be slid proximally with respect to filter member 130 to remove filter member 130 from sleeve 132. Alternatively, a filter member removal device such as push rod 360 (FIG. 8D) may be used to remove filter member 130 from sleeve 132 in the manner discussed below. The collected tissue samples may then be removed from the exterior surface 145 of the filter 142.

Figure 8C:
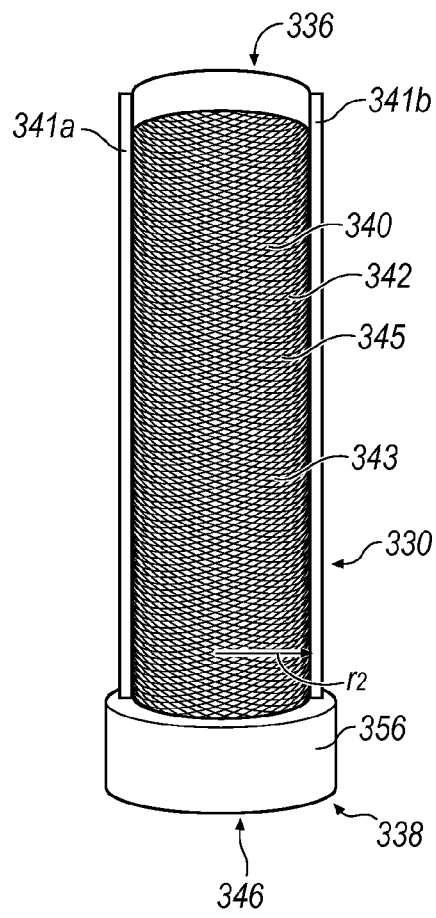
FIG. 8C is a plan view of an alternate embodiment of a tissue collection filter member suitable for use with the tissue collection device of FIG. 8B in which the filter comprises a reinforced mesh.

Referring to FIG. 8C, an alternate embodiment of a filter member 330 suitable for use with sleeve 132 and housing 122 is depicted. Filter member 330 comprises filter 342 and base 356. Filter 342 comprises a generally cylindrical mesh body 343, longitudinally-extending supports 341a and 341b, and a closed distal end 336. Interior passage 340 allows filtered fluids to pass through filter 342 and out of outlet port 346. Base 356 cooperates with sleeve 132 in the same manner as base 156 of FIGS. 8A and 8B and may include a non-smooth proximal facing surface of the type described previously. In the embodiment of FIG. 8C, closed distal end 336 is a generally thin cylindrical structure. However, it may also be conical, frusto-conical, polygonal, pyramidal, etc. The mesh 343 may be constructed from a variety of mesh materials. However, in one exemplary embodiment, mesh 343 is a hemodialysis grade 240 micron mesh. Supports 341a and 341b and closed distal end 336 are preferably formed from a medical grade resin of the type described previously. Supports 341a and 341b are preferably provided around the circumference of mesh 343. The number and size of supports 341a and 341b are preferably selected to prevent mesh 343 from collapsing when a vacuum pressure is applied to interior passage 340 of filter 342. In the embodiment of FIG. 8C, two (2) supports 341a and 341b are positioned diametrically opposite one another. In another embodiment, four (4) supports are provided comprising two (2) pairs of supports, wherein the supports comprising each pair are positioned diametrically opposite one another. When filter member 330 is installed in sleeve 342 in the manner that filter member 130 of FIG. 8B is installed, exterior surface 345 is preferably not in direct fluid communication with sleeve proximal end opening 154 such that unfiltered fluids are substantially prevented from exiting sleeve 132 therethrough. A seal 351 (not shown) may be disposed about base 356 to prevent tissue and fluids from leaking around base 356.

Figure 8D:
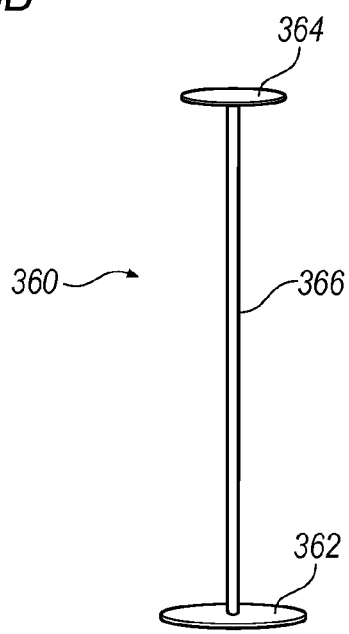
FIG. 8D is a plan view of a push rod suitable for removing a tissue filter member from a tissue filter member sleeve.

In certain exemplary embodiments, a device is provided to facilitate the removal of filter member 130 from sleeve 132. In one embodiment, depicted in FIG. 8D, a push rod 360 is provided. Push rod 360 is a generally rigid member comprising a metal or plastic material. Shaft 366 is generally cylindrical and connects a user deployment end 362 and a filter member contact end 364. User deployment end 362 is a thin cylindrical structure and is configured so that the user's index and middle fingers are positioned on its distal facing surface, while the user's thumb is positioned on its proximal facing surface. Filter member contact end 364 is also a thin cylindrical structure having a diameter that is preferably less than the diameter of user deployment end 362. In one exemplary embodiment, the diameter of filter member contact end 364 is selected to that it can be inserted into sleeve proximal end opening 154. Once inserted, the user advances push rod 360 in distal direction D to advance filter member 130 in the distal direction with respect to sleeve 132. User deployment end 362 preferably has a diameter greater than that of sleeve proximal end opening 154 so that as push rod 360 is advanced distally, user deployment end 362 eventually contacts the proximal facing surface of proximal end sleeve opening 154. As a result, push rod 360 cannot be fully inserted into sleeve 132. To facilitate the removal of push rod 360 from sleeve 132, an additional feature such as a small handle or other feature that can be grasped by a user can be included on user deployment end 362. In one embodiment, a handle extending away from push rod 360 is attached to user deployment end 362 and projects away from sleeve 132 when push rod 360 is fully inserted in sleeve 132. The handle may have a variety of sizes and geometries. As indicated in FIG. 8D, in an exemplary embodiment, shaft 366 is at least as long as filter member 130 to facilitate its complete removal from sleeve 132. In certain embodiments, filter member 130, sleeve 132, and push rod 360 may be provided as a kit.

Figure 9:
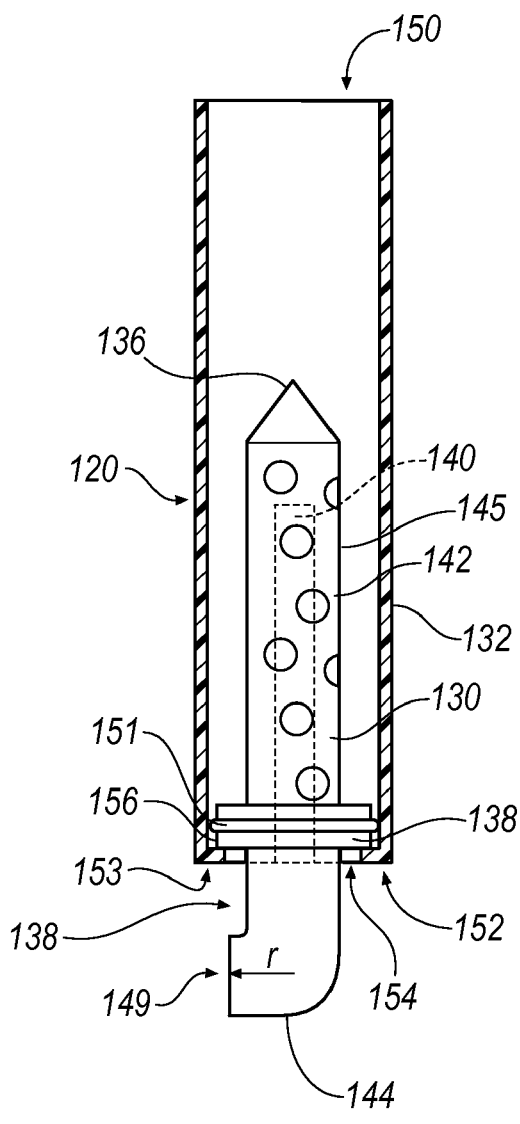
FIG. 9 is an alternate embodiment of a tissue sample collection device with an external vacuum fitting.
Figure 10:
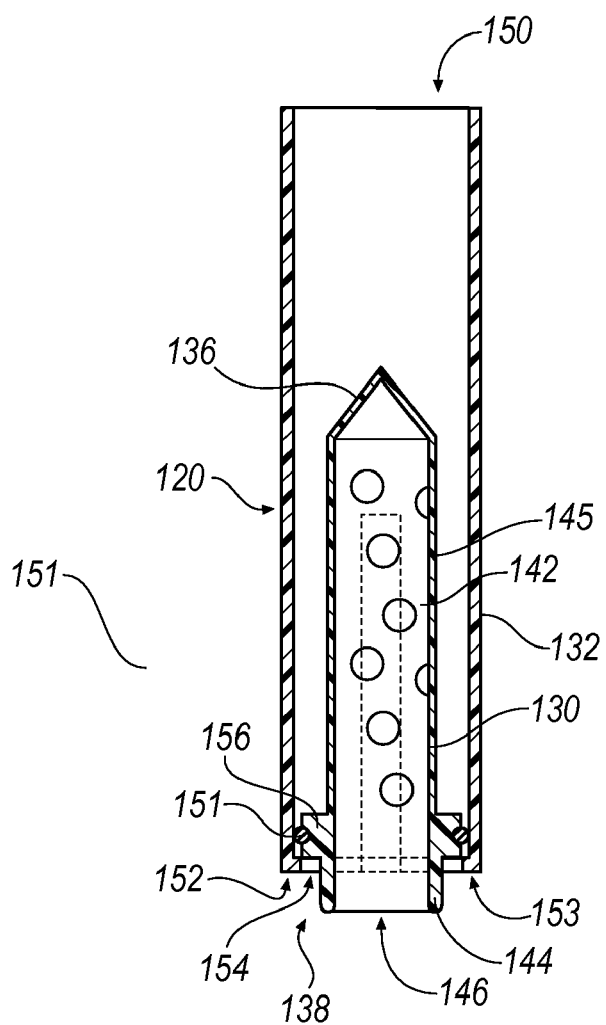
FIG. 10 is another alternate embodiment of a tissue sample collection device with an external vacuum fitting.

The tissue collection devices described herein may be configured for connection to a source of vacuum in a variety of different ways. Referring to FIGS. 9 and 10, tissue collection devices 120 are provided which are modified versions of the device 120 shown in FIG. 8B. Like numerals in the drawings refer to like parts. As in the embodiment of FIG. 8B, tissue collection sample device 120 includes a filter member 130 and a sleeve 132 of the type described previously. Filter member 130 comprises a filter 142, base 156, and vacuum source fitting 144. Vacuum source fitting 144 is located at proximal end 138 of filter member 130. In the embodiment of FIG. 9, vacuum source fitting 144 is shaped as an elbow with a hollow interior that is connected to base 156. Vacuum source fitting 144 may be integrally formed with filter member 130 or separately attachable to it. If fitting 144 is integrally formed with filter member 130, the radial projection r of the elbow is preferably less than the radius of open distal sleeve end 150 and sleeve proximal end opening 154 to ensure that the filter member can be slid into sleeve open distal end 150 with fitting 144 projecting out of sleeve proximal end opening 154. Fitting 144 may have threads formed on the interior or exterior of its free end 149 for mating with a vacuum source fitting. The hollow interior of fitting 144 is in fluid communication with internal passageway 140 of filter member 130 to allow fluids to be aspirated therethrough and out of free end 149. As FIG. 9 indicates, when tissue collection device 120 is configured for tissue collection, base 156 is seated against lip 153, and fitting 144 projects away from sleeve 132 in the proximal direction as well as in a radially outward direction.

In the embodiment of FIG. 10, vacuum source fitting 144 is formed as an axially depending flange that extends in the proximal direction away from base 156 of filter member 130. Fitting 144 may be separately attachable to filter member 130, but is preferably integrally formed with it. Fitting 144 may have internal or external threads to facilitate connection to a source of vacuum. As FIG. 10 indicates, when tissue collection device 120 is in a tissue collection configuration, base 156 is seated against sleeve lip 153, and fitting 144 projects outward and away from sleeve 132 in the proximal direction. Although not separately depicted, the filter member structures of FIGS. 9 and 10 may be used with the mesh filter 342 depicted in FIG. 8C.

It will be appreciated that the tissue sample collection devices and assemblies described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed as new and desired to be protected by Letters Patent of the United States is:

1. A tissue sample collection device, comprising:
    a sleeve having an interior, an open proximal end and an open distal end; and
    a filter member having a length, an open proximal end, and comprising a filter extending along at least a portion of the length of the filter member, wherein the filter member has an internal passageway extending along a least a portion of the length of the filter member, the filter comprises an exterior tissue collecting surface, the filter is substantially permeable to fluids and substantially impermeable to tissue samples, wherein when the filter is disposed in the sleeve, the device defines a fluid flow path from the open distal end of the sleeve to the internal passageway of the filter member, out of the open proximal end of the filter member, and out of the open proximal end of the sleeve, and further wherein the filter is removable through the distal end of the sleeve;
    wherein the filter member is connected to the sleeve such that the device has a tissue collection configuration and a tissue retrieval configuration, and when the device is in the tissue collection configuration, the filter is disposed entirely within the sleeve, and when the device is in the tissue retrieval configuration, the filter member remains connected to the sleeve and extends through the distal end of the sleeve to permit access to the filter member; and
    wherein the sleeve is slidably adjustable along the length of the filter member to change the configuration of the device from the tissue collection configuration to the tissue retrieval configuration, the sleeve including a longitudinally extending inner surface configured to maintain engagement with the filter member as the sleeve is adjusted from the tissue collection configuration to the tissue retrieval configuration, the longitudinally extending inner surface defining a length sufficiently large that the longitudinally extending inner surface remains in engagement with the filter member at least until the filter member extends through the distal end of the sleeve to permit access to the filter.

2. The tissue sample collection device of claim 1, wherein the filter comprises a mesh material.

3. The tissue sample collection device of claim 1, wherein the filter is generally rigid and comprises holes at a plurality of spaced apart locations.

4. The tissue sample collection device of claim 1, wherein the filter member comprises a proximal end and a distal end, and when the filter is disposed in the sleeve, the device has an annular space defined between the distal end of the filter member and the sleeve.

5. The tissue sample collection device of claim 1, wherein the filter is not insertable through the proximal end of the sleeve.

6. The tissue sample collection device of claim 1, wherein when the device is in the tissue retrieval configuration, the filter projects away from the open distal end of the sleeve.

7. The tissue sample collection device of claim 1, wherein when the device is in the tissue collection configuration, the proximal end of the sleeve is spaced apart from the proximal end of the filter member by a first distance along a longitudinal axis of the sleeve, when the device is in the tissue retrieval configuration, the proximal end of the sleeve is spaced apart from the proximal end of the tissue filter member by a second distance along the longitudinal axis of the sleeve, and the first distance is greater than the second distance.

8. A tissue sample collection assembly, comprising the tissue sample collection device of claim 1 and a housing, wherein the housing has a cavity shaped to receive the tissue sample collection device when the tissue sample collection device is in the tissue collection configuration.

9. The tissue sample collection assembly of claim 8, wherein the housing partially encloses a perimeter of the tissue sample collection device along at least a portion of the length of the tissue sample collection device.

10. The tissue sample collection device of claim 1, wherein the proximal end of the sleeve has an opening of a first diameter, the distal end of the sleeve has an opening of a second diameter, and the first diameter is less than the second diameter.

11. The tissue sample collection device of claim 10, wherein the filter member has a maximum diameter that is greater than the first diameter.

12. The tissue sample collection device of claim 1, wherein the proximal end of the sleeve has a lip, the filter member has a first radial flange adjacent the filter, and when the radial flange abuts the lip, the filter is disposed entirely within the sleeve.

13. The tissue sample collection device of claim 12, wherein the filter member has a second radial flange between the first radial flange and the proximal end of the filter member, and when the second radial flange abuts the lip, the filter projects away from the sleeve in the distal direction.

14. A tissue sample collection assembly, comprising:
a tissue sample collection device, including:
a sleeve having an interior, an open proximal end and an open distal end; and
a filter member having a length, an open proximal end, and comprising a filter extending along at least a portion of the length of the filter member, wherein the filter member has an internal passageway extending along a least a portion of the length of the filter member, the filter comprises an exterior tissue collecting surface, the filter is substantially permeable to fluids and substantially impermeable to tissue samples, wherein when the filter is disposed in the sleeve, the device defines a fluid flow path from the open distal end of the sleeve to the internal passageway of the filter member, out of the open proximal end of the filter member, and out of the open proximal end of the sleeve, and further wherein the filter is removable through the distal end of the sleeve;
wherein the filter member is connected to the sleeve such that the device has a tissue collection configuration and a tissue retrieval configuration, and when the device is in the tissue collection configuration, the filter is disposed entirely within the sleeve, and when the device is in the tissue retrieval configuration, the filter member remains connected to the sleeve and extends through the distal end of the sleeve to permit access to the filter member; and
wherein the sleeve is slidably adjustable along the length of the filter member to change the configuration of the device from the tissue collection configuration to the tissue retrieval configuration, the sleeve including a longitudinally extending inner surface configured to maintain engagement with the filter member as the sleeve is adjusted from the tissue collection configuration to the tissue retrieval configuration, the longitudinally extending inner surface defining a length sufficiently large that the longitudinally extending inner surface remains in engagement with the filter member at least until the filter member extends through the distal end of the sleeve to permit access to the filter; and
a housing, wherein the housing has a cavity shaped to receive the tissue sample collection device when the tissue sample collection device is in the tissue collection configuration;
wherein the housing has a longitudinal axis and includes a lid, the lid is pivotable about a pivot axis while connected to the housing, the pivot axis substantially perpendicular to the longitudinal axis of the housing, the lid defining a port, and when the tissue sample collection device is installed in the housing, the open distal end of the sleeve is in fluid communication with the port.

15. A tissue sample collection device, comprising:
a filter member having a filter;
a sleeve having an open proximal end and an open distal end, the sleeve being attached to the filter member such that the sleeve is slidably adjustable between a first relative position with respect to the filter member in which the filter is disposed entirely within the sleeve, and a second relative position with respect to the filter member in which the filter projects through the distal end of the sleeve and away from the distal end of the sleeve to permit access to the filter, wherein the filter member remains connected to the sleeve in the second relative position;
wherein the sleeve is slidably adjustable along the length of the filter member to change the configuration of the device from the first relative position to the second relative position, the sleeve including a longitudinally extending inner surface configured to maintain engagement with the filter member as the sleeve is adjusted from the first relative position to the second relative position, the longitudinally extending inner surface defining a length sufficiently large that the longitudinally extending inner surface remains in engagement with the filter member at least until the filter member extends through the distal end of the sleeve to permit access to the filter; and
wherein the filter member comprises an open proximal end, an internal passageway in fluid communication with the open proximal end of the filter member, and when the sleeve is in the first relative position with respect to the filter member, an annular space is defined between the filter and the sleeve, wherein the filter is permeable to fluid located in the annular space.

16. The tissue sample collection device of claim 15, wherein the filter member has a first radial flange adjacent the filter, and the sleeve has a lip at the proximal end of the sleeve, and when the first radial flange abuts the lip, the sleeve is in the first relative position with respect to the filter member.

17. The tissue sample collection device of claim 16, wherein the filter member has a second radial flange between the first radial flange and the proximal end of the filter, and when the lip abuts the second radial flange, the sleeve is in the second relative position with respect to the filter member.

18. The tissue sample collection device of claim 17, wherein the second radial flange has a diameter, the open proximal end of the sleeve defines an opening having a diameter, and the second radial flange diameter is greater than the sleeve proximal end opening diameter.

19. The tissue sample collection device of claim 16, wherein the first radial flange has a diameter, the open proximal end of the sleeve defines an opening having a diameter, and the first radial flange diameter is greater than the sleeve proximal end opening diameter.

20. The tissue sample collection device of claim 16, wherein when the sleeve is in the first relative position with respect to the filter member, the first radial flange is disposed within the sleeve.

* * * * *